US012612878B2

(12) United States Patent
Obrist

(10) Patent No.: US 12,612,878 B2
(45) Date of Patent: Apr. 28, 2026

(54) METHOD OF OPERATING AN INTERNAL COMBUSTION ENGINE OF A TRUCK OR OMNIBUS

(71) Applicant: OBRIST TECHNOLOGIES GMBH, Lustenau (AT)

(72) Inventor: Frank Obrist, Bregenz (AT)

(73) Assignee: OBRIST TECHNOLOGIES GMBH, Lustenau (AT)

( * ) Notice: Subject to any disclaimer, the term of this patent is extended or adjusted under 35 U.S.C. 154(b) by 0 days.

(21) Appl. No.: 18/272,003

(22) PCT Filed: Jan. 12, 2022

(86) PCT No.: PCT/EP2022/050558
§ 371 (c)(1),
(2) Date: Aug. 30, 2023

(87) PCT Pub. No.: WO2022/152757
PCT Pub. Date: Jul. 21, 2022

(65) Prior Publication Data
US 2024/0003305 A1 Jan. 4, 2024

(30) Foreign Application Priority Data

Jan. 13, 2021 (DE) .......................... 102021100545.0

(51) Int. Cl.
*F02D 19/06* (2006.01)
*B60K 6/24* (2007.10)
(Continued)

(52) U.S. Cl.
CPC ............ *F02D 19/0644* (2013.01); *B60K 6/24* (2013.01); *C07C 29/152* (2013.01); *F02B 63/04* (2013.01);
(Continued)

(58) Field of Classification Search
CPC .... F02D 19/0644; F02B 63/04; F02B 75/225; F02B 2075/1808; B60K 6/24;
(Continued)

(56) References Cited

U.S. PATENT DOCUMENTS 6,571,747 B1 * 6/2003 Gerstweiler ........ C07C 29/1518
123/3
2002/0025457 A1 2/2002 Dodd et al.
(Continued)

FOREIGN PATENT DOCUMENTS

DE 19714512 A1 10/1998
DE 102010048356 A1 * 12/2011 ............. G08C 17/00
(Continued)

OTHER PUBLICATIONS https://www.dot.state.pa.US/public/pdf/InfoBridge/Approximate%20vehicle%20weights.pdf (Year: 2013).*
(Continued)

*Primary Examiner* — Syed O Hasan
(74) *Attorney, Agent, or Firm* — Cesari and McKenna, LLP

(57) ABSTRACT

The disclosure relates to a method for operating an internal combustion engine of a truck or omnibus, in particular a truck or omnibus with a permissible total mass of at least 3.5 tonnes, wherein (i) an electrolysis unit for the production of hydrogen, water is split into hydrogen and oxygen, (ii) a carbon dioxide sorption unit extracts carbon dioxide from the ambient air, (iii) the hydrogen and the carbon dioxide are fed to a methanol synthesis unit for the production of methanol, and are synthesised therein to methanol, (iv) a photovoltaic unit absorbs solar energy and converts it into electrical energy. The electrolysis unit, the carbon dioxide sorption unit and the methanol synthesis unit are powered by the electrical energy generated in the photovoltaic unit. The
(Continued)

methanol produced is transported by means of a distributor system to at least one tank of the truck or omnibus, and is supplied from the tank as required to the internal combustion engine, and therein is combusted to generate mechanical energy.

12 Claims, 5 Drawing Sheets

(51) Int. Cl.
C07C 29/152 (2006.01)
F02B 63/04 (2006.01)
F02B 75/22 (2006.01)
F02B 75/18 (2006.01)
(52) U.S. Cl.
CPC .... F02B 75/225 (2013.01); F02B 2075/1808 (2013.01)
(58) Field of Classification Search
CPC ... C07C 29/152; C07C 29/1516; C02F 1/265; B01D 53/1475
See application file for complete search history.

(56) References Cited

U.S. PATENT DOCUMENTS

| | | | | |
|---|---|---|---|---|
| 2009/0012332 A1* | 1/2009 | Shaw | .................... | F25J 3/0257 |
| | | | | 568/840 |
| 2012/0091730 A1* | 4/2012 | Stuermer | ................ | C25B 15/08 |
| | | | | 290/1 R |
| 2012/0198884 A1* | 8/2012 | Golben | .................... | C10L 1/04 |
| | | | | 422/600 |
| 2014/0290596 A1 | 10/2014 | Cohn et al. | | |
| 2019/0084444 A1* | 3/2019 | Ge | .......................... | B60L 50/15 |

FOREIGN PATENT DOCUMENTS

| | | | | |
|---|---|---|---|---|
| DE | 102013109459 A1 * | 4/2014 | ......... | F02M 25/0818 |
| DE | 102014115041 A1 | 4/2016 | | |
| DE | 102018125876 A1 | 4/2020 | | |
| EP | 1225073 A2 | 7/2002 | | |
| JP | 2013185528 A * | 9/2013 | ......... | F02M 25/0818 |
| WO | WO-2013/055673 A1 | 4/2013 | | |
| WO | 2014191074 A1 | 12/2014 | | |
| WO | WO-2018112654 A1 | 6/2018 | | |

OTHER PUBLICATIONS

"Alternate Energy", Karl Vadaszffy, Engine Technology International. com, Sep. 2020, https://www.obrist.at/wp-content/uploads/2021/03/engine powertrain.pdf>, 1 page.
"E-Fuels: Towards a More Sustanable Future for Truck Transport, Shipping and Aviation", Kranenburg et al., Jul. 2020, 17 pages.
"Fuel from Wind and Sun", Anonymous, Dec. 17, 2020, https://www.siemens-energy.com/global/en/news/magazine/2020/fuel-from-wind-and-s un.html, 11 pages.
German Search Report, German Patent Application No. 10 2021100 545.0, mailed Aug. 2, 2021, 7 pages.
PCT Notification of Transmittal of the International Search Report and the Written Opinion of the International Searching Authority, or the Declaration, International Searching Authority, International Application No. PCT/EP2022/050558, mailed Jun. 23, 2022, 21 pages.
"Powering the Future with Liquid Sunshine", Choon Fong Shih et al., *Joule*, Cell Press, Oct. 1, 2018, pp. 1925-1949.
"Technology Comparison—A Renewable Energy Supply for Transport", by Dr. Michael Sterner et al., FVEE annual conference Berlin, Oct. 12, 2010, 14 pages.
Wikepedia—Methanol as Fuel, https://cle.wilupeclia.org/w/index.php7title-M, Aug. 2, 2021, 12 pages, translation 10 pages.

* cited by examiner

METHOD OF OPERATING AN INTERNAL COMBUSTION ENGINE OF A TRUCK OR OMNIBUS

CROSS REFERENCE TO RELATED APPLICATIONS

This application is the National Stage of International Application No. PCT/EP2022/050558, filed Jan. 12, 2022, which claims the benefit of German Patent Application No. 102021100545.0 filed on Jan. 13, 2021. The contents of both applications are hereby incorporated by reference in their entirety.

TECHNICAL FIELD

The invention relates to the utilisation of methanol, in particular produced in a globally $CO_2$ neutral manner, as a fuel for an internal combustion engine of a truck or omnibus. The invention also relates to a method for operating an internal combustion engine of a truck or an omnibus, and to a truck or an omnibus with a sustainable drive system.

BACKGROUND

Mobility, especially of goods, is one of the most important prerequisites for economic success, employment, and prosperity. At the same time, however, mobility also means a heavy environmental burden due to transport systems, and to the continuous increase in global transport volumes over the past decades. The efficiency of combustion engines has indeed improved significantly and they have become cleaner and quieter. However, due to the increased transport volumes, large quantities of greenhouse gases and air pollutants continue to be produced and released into the atmosphere. With the increase in transport volumes, the energy consumption of transport in Germany, for example, has more than tripled since 1960. Currently, transport is responsible for about one fifth of the greenhouse gas emissions in Germany. What applies to environmental and climate pollution in Germany also applies to the global climate situation, which suffers significantly from the combustion of fossil fuels in road transport.

In order to counteract this negative development and limit climate damage, the Climate Protection Plan 2050 adopted in Germany, for example, aims to reduce annual greenhouse gas emissions in the transport sector from the current level of around 160 million tonnes of $CO_2$ equivalents to between 95 and 98 million tonnes of $CO_2$ equivalents in 2030. The European Commission is also pursuing the goal of decarbonising the European mobility system by the year 2050, that is to say, making it greenhouse gas neutral. Success depends on whether the measures taken to achieve these goals are supported by broad sections of society, and on whether these measures are economical. The central goal is to ensure that the mobility needs of broad sections of the population today are met in the future in a manner that is as environmentally compatible as possible. This means that a successful mobility solution must not only be technically feasible and target-oriented, but must also be measured against the costs of current mobility solutions.

In addition to the fuel cell technology and electrification of vehicle drives of known art, the utilisation of synthetically produced fuels is an important component in the development of new mobility concepts. Here methanol plays an important role as a fuel. Methanol is produced by synthesising hydrogen and carbon dioxide, which are obtained regeneratively, that is to say, in a greenhouse gas-neutral manner. For this purpose, a method is described in WO 2018/112654 A1, for example, in which hydrogen is produced by electrolysis, and carbon dioxide is obtained by direct separation out from the ambient air; these are utilised to produce methanol. However, the method of known art is not suitable for providing an energy source in sufficient quantity with the necessary economic efficiency to reduce climate pollution to a noticeable extent, and which at the same time meets current mobility needs.

In the electrification of drive trains, the focus is mainly on passenger cars, as these can achieve a sufficient range with the accumulator technologies available at the present time. However, for heavier vehicles, especially trucks or omnibuses, large accumulators are necessary, which at best only allow a sufficient range for short distances. In any event, the payload suffers, because the accumulators significantly increase the unladen weight of the vehicles. For long-distance trucks and coaches, this technology is therefore not economically viable at the present time.

SUMMARY

The invention is based on the object of providing a possible means for the operation of trucks and omnibuses in a climate-friendly manner, without a significant reduction of their payload. Furthermore, it is the object of the invention to specify a climate-friendly operating method for trucks and omnibuses, together with a truck or an omnibus with a climate-friendly drive system.

In accordance with the invention, this object is achieved by an operating method in accordance with claim 1, a utilisation in accordance with claim 5, and a truck or omnibus in accordance with claim 7.

Thus, the invention is based on the concept of specifying a utilisation of methanol as a fuel for an internal combustion engine of a truck or an omnibus, in particular a truck or an omnibus with a maximum permissible mass of at least 3.5 tonnes. In accordance with the invention, the methanol is produced in a process in which:

in an electrolysis unit for the production of hydrogen, water is split into hydrogen and oxygen, a carbon dioxide sorption unit extracts carbon dioxide from the ambient air, the hydrogen and the carbon dioxide are fed to a methanol synthesis unit for the production of methanol, and are synthesised therein to methanol, and a photovoltaic unit absorbs solar energy and converts it into electrical energy.

The electrolysis unit, the carbon dioxide sorption unit, and the methanol synthesis unit, are thereby operated by the electrical energy generated in the photovoltaic unit.

By the utilisation of methanol produced by the process steps described above, a truck or omnibus can be operated in a climate-friendly manner, in particular in a climate-neutral manner, while the payload remains essentially unchanged compared to that of conventionally powered trucks or omnibuses. In this respect, this technology offers the potential for achieving climate-neutral mobility and goods transport. The methanol, which is preferably produced in regions with high annual solar radiation in a $CO_2$-neutral manner, for example in Saudi Arabia, Oman, Australia, or other regions that have continuously high solar radiation, is easy to transport and store. Methanol is therefore particularly suitable as an energy source that can be utilised worldwide.

Furthermore, methanol has a sufficient energy density such that it can logically be utilised for freight transport or omnibus transport, especially for longer journeys. Refuelling is also much faster than the charging of an accumulator, so that such a drive concept can be expected to be more widely accepted in the operation of heavy goods vehicles and omnibuses, which is strongly driven by economic considerations. This is especially true for the operation of heavy long-distance trucks or coaches. In this respect, it is preferable if the methanol is utilised as a fuel for an internal combustion engine of a heavy goods vehicle or an omnibus with a permissible total mass of at least 3.5 tonnes, in particular at least 5 tonnes, in particular at least 7.5 tonnes, in particular at least 10 tonnes, in particular at least 15 tonnes.

In a preferred form of embodiment, it is envisaged that the water is first desalinated in a seawater desalination unit and then fed to the electrolysis unit, wherein the seawater desalination unit is operated mainly, in particular completely, by the electrical energy generated in the photovoltaic unit.

The photovoltaic unit can have a power, in particular a peak power, of at least 1.0 gigawatts, in particular at least 1.3 gigawatts, in particular at least 1.5 gigawatts, for the conversion of solar energy into electricity. The seawater desalination unit for the production of desalinated water preferably has an intake capacity of at least 900,000 tonnes of seawater per year. For the production of hydrogen, the electrolysis unit can be connected to the seawater desalination unit for the supply of water, in particular desalinated water, through at least one pipeline. The carbon dioxide sorption unit for the sorption of carbon dioxide from ambient air can have an extraction capacity of at least 400,000 tons of carbon dioxide per year, in particular at least 600,000 tons of carbon dioxide per year, from ambient air. For the production of methanol the methanol synthesis unit can be connected to the electrolysis unit for the supply of hydrogen through at least one pipeline, and to the carbon dioxide sorption unit for the supply of carbon dioxide through at least one pipeline.

The seawater desalination unit, the electrolysis unit, the carbon dioxide sorption unit, and the methanol synthesis unit, can each be connected to the photovoltaic unit for purposes of power supply, and arranged in an area of the plant contiguous with the photovoltaic unit.

It is particularly preferred if the methanol is produced in a region with high solar irradiation, in particular a solar irradiation of more than 2,000 kWh/m2a, in particular more than 2,300 kWh/m2a, in particular more than 2,500 kWh/m2a. For this purpose, the photovoltaic unit can be customised to receive at least 1,500 kWh/m2a, in particular at least 2,000 kWh/m2a, in particular at least 2,300 kWh/m2a, in particular at least 2,500 kWh/m2a, in particular at least 2,700 kWh/m2a of solar energy.

The methanol synthesis unit can have a delivery capacity of at least 300,000 tonnes, in particular at least 450,000 tonnes, of regeneratively-produced methanol per year. A delivery capacity of 450,000 tonnes of regeneratively-produced methanol per year is particularly preferred.

The process-relevant units of the system can each be connected to the photovoltaic unit for purposes of power supply, and arranged, together with the photovoltaic unit, in a contiguous plant area. This means that the individual units are arranged in spatial proximity to each other and are consolidated in a unitary plant. It is not necessary for the plant area to be enclosed. The individual units can, for example, be separated from each other by supply roads that run through the plant. This ensures that the transport of material flows and the power supply between the units takes place with the lowest possible losses.

In addition, this ensures that the plant as a whole is constructed in such a manner that it can be positioned in an optimal manner for the location, and operated in an autonomous manner. The particular advantage of the combination of the seawater desalination unit and the photovoltaic unit is that the plant can be set up in geographical regions, such as in the Middle East or Africa, which have both high solar irradiation and access to seawater, so that, on the one hand, the supply of energy to the plant by the photovoltaic unit and, on the other hand, the provision of sufficiently large quantities of water for the electrolysis unit, is made possible in an economical manner.

By means of the power supply to the electrolysis unit, which is carried out exclusively by the photovoltaic unit, the plant produces hydrogen in a regenerative manner. The carbon dioxide required for methanol production can be extracted from the ambient air of the plant by the carbon dioxide sorption unit. By the combination of the two units in the plant, methanol production takes place in a regenerative manner without the generation of carbon dioxide. Instead, by the removal of the carbon dioxide from the ambient air, the carbon dioxide concentration in the atmosphere is reduced. The plant is thus suitable to be a part of a climate-neutral energy system that forms a global carbon dioxide cycle, with regeneratively-produced methanol as the energy source. This means that the carbon dioxide extracted from the ambient air does not have to be disposed of, or dumped, as is usually the case, for example in the storage of known art of carbon dioxide in deep rock strata, although this is not ruled out as an additional measure, for example. The carbon dioxide sorbed from the ambient air is a valuable substance that is utilised in the plant to produce a synthetic fuel, namely methanol, and can thus be fed into a carbon dioxide cycle.

The economic efficiency of the measures taken, which is necessary for the implementation of the aforementioned climate goals, is made possible by the plant. Compared to the production and utilisation of hydrogen for fuel cells, the conversion losses do indeed increase as a result of the additional process steps required for the synthesis of methanol. However, these are offset by much greater economic advantages with regard to the global infrastructure costs that are incurred in the combustion of methanol, compared to those incurred in purely electrical drives or fuel cell technology. The costs for expensive charging stations or for the technically complex storage of hydrogen do not apply to the combustion of regeneratively-produced methanol. The storage and transport of methanol require no special measures, and are comparable to the handling of conventional fuels. Another advantage of regeneratively-produced methanol, compared to hydrogen or batteries as energy sources, is that the energy density of methanol with 4.35 kWh/litre is much higher than that of high-pressure hydrogen (800 bar) with 1.25 kWh/litre, liquid hydrogen with 2.36 kWh/litre, and batteries with 0.5 kWh/litre.

A comparison of current energy prices, which is intended to give an approximate indication of the energy costs of a plant for the regenerative production of methanol, shows that the photovoltaic unit envisaged as part of the plant is an important component not only for producing synthetic fuel in a regenerative manner, but also for producing it so economically that the fuel can prevail in the competitive battle with other energy sources. The energy prices for wind energy (2.39 EURct/kWh) and hydropower energy (1.71

EURct/kWh) are currently (2020) already far below the energy prices for fossil fuels and, of course, nuclear energy. However, the energy price for electricity production by means of photovoltaics is even lower, at 1.14 EURct/kWh for electricity produced in regions with high and long solar irradiation, such as the Middle East or Africa. Photovoltaic plants with an installed capacity of 2 gigawatts, for example, already exist there and are able to produce electricity at the aforementioned price.

In this respect, the plant can be designed to be installed in regions in which large areas cannot be utilised for agriculture because they are deserts or steppes, so that sufficiently large areas are available for a correspondingly large photovoltaic unit. Preferably, the power, in particular the peak power, of the photovoltaic unit is at least 1.0 gigawatts, in particular at least 1.3 gigawatts, in particular at least 1.5 gigawatts. The seawater desalination unit for producing desalinated water is designed for an intake capacity of at least 900,000 tonnes of seawater per year. The carbon dioxide sorption unit is preferably designed for an extraction capacity of at least 400,000 tonnes of carbon dioxide per year, in particular at least 600,000 tonnes of carbon dioxide per year, from the ambient air. The seawater desalination unit and the carbon dioxide sorption unit are thus matched in terms of performance to the methanol synthesis unit, which has a delivery capacity of at least 300,000 tonnes, in particular of at least 450,000 tonnes, of regeneratively-produced methanol per year. The electricity required for the power supply to the aforementioned process units, including the electrolysis unit, is provided by the photovoltaic unit, which is customised to receive at least 1,500 kWh/m2a, in particular at least 2,000 kWh/m2a, in particular at least 2,300 kWh/m2a, in particular at least 2,500 kWh/m2a, in particular at least 2,700 kWh/m2a of solar energy. The unit kWh/m2a means kilowatt hours per square metre and per year.

The plant can form the basic unit for a larger plant complex with a plurality of plants that are designed in accordance with the plant described above. This allows the production of methanol in larger quantities to be scaled up so that, with a corresponding number of plants, a large energy demand, in particular the entire energy demand of the world's population, can be covered.

The invention is further based on the concept of providing a method of operating an internal combustion engine of a truck or omnibus, in particular a truck or omnibus with a maximum permissible mass of at least 3.5 tonnes, in which:

in an electrolysis unit for the production of hydrogen, water is split into hydrogen and oxygen, a carbon dioxide sorption unit extracts carbon dioxide from the ambient air, the hydrogen and the carbon dioxide are fed to a methanol synthesis unit for the production of methanol, and are synthesised therein to methanol, a photovoltaic unit absorbs solar energy and converts it into electrical energy.

In accordance with the invention, the electrolysis unit, the carbon dioxide sorption unit, and the methanol synthesis unit, are operated by the electrical energy generated in the photovoltaic unit, wherein the methanol produced is transported by means of a distributor system to at least one tank of the truck or omnibus, and is supplied from the tank to the internal combustion engine as required, and therein is combusted to generate mechanical energy.

The distributor system is preferably customised to distribute the regeneratively-produced methanol from the delivery device to end users for the combustion of the regeneratively-produced methanol. The distributor system is designed, for example, in the form of a logistics network in which the methanol is transported in tankers to filling stations. At the filling stations, the tank, in particular a methanol fuel tank, of the truck or omnibus can be filled with methanol.

The distributor system can be preceded by a transport system that is connected, or can be connected, to the methanol synthesis unit of the plant in accordance with the invention, and is customised to transport the methanol regeneratively-produced by the methanol synthesis unit from the methanol synthesis unit to at least one delivery device. The transport system can be stationary or mobile, and can comprise, for example, pumps and pipelines, or transport by tankers. Transport systems known per se, for example for the transport of crude oil, can be utilised. The delivery device can be a storage tank in a port, or at a pumping station.

The combustion of the regeneratively-produced methanol produces carbon dioxide, which is released into the atmosphere. The desired carbon dioxide cycle is closed by the carbon dioxide sorption unit, which, directly or indirectly, separates out the carbon dioxide that has entered the atmosphere from the latter once again, and uses it in the methanol production process. The methanol produced in this manner, and thus the carbon dioxide utilised for its production, is returned to the carbon dioxide cycle.

The fact that the trucks or omnibuses using the methanol and the place where the methanol is produced are spatially far apart from each other is irrelevant, since what is at stake is the overall balance of carbon dioxide in the atmosphere, which remains constant by the formation of the closed carbon dioxide cycle. It is even possible to reduce the carbon dioxide concentration in the atmosphere if the carbon dioxide sorption unit removes an excess of carbon dioxide from the atmosphere, which is not returned to the cycle by methanol as an energy source. The excess carbon dioxide is then disposed of elsewhere, for example by storing it in deep rock strata, as is already the practice in Iceland.

In a preferred form of embodiment of the method in accordance with the invention, the water is desalinated in a seawater desalination unit and then fed to the electrolysis unit, wherein the seawater desalination unit is operated mainly, in particular completely, by means of the electrical energy generated in the photovoltaic unit.

For an insight into the invention, it is essential to understand that the methanol is utilised as the main fuel in the internal combustion engine. That is to say, the methanol does not take the form of an additive that is mixed with another fuel. Rather, the methanol is utilised in such a manner that the combustion engine is operated solely with the latter.

The internal combustion engine is preferably a reciprocating piston engine operated with a compression ratio of at least 14:1, in particular at least 16:1, in particular at least 18:1, in particular at least 20:1. In particular, the reciprocating piston engine can be a four-stroke Otto cycle engine.

Currently, the diesel engine has a high market share in trucks and omnibuses. However, the utilisation of methanol makes it possible to operate an Otto cycle engine with an otherwise unusually high compression ratio. With the high compression, a significant increase in efficiency is achieved, especially in an operation with a balanced combustion air ratio ($\lambda=1$). This enables a high power to be achieved in a four-stroke Otto cycle engine with low fuel consumption. At the same time, a large part of the very complex exhaust gas after-treatment required in diesel engines is omitted, which saves space and weight and thus further increases the efficiency of the truck or omnibus. In particular, this provides space for the integration of a drive battery for a hybrid drive train into the truck or omnibus, while substantially maintaining the payload.

Part of the methanol can be split in a splitting unit into a synthesis gas, which comprises or consists of hydrogen and carbon monoxide, and the synthesis gas alone, or together with the methanol, can be fed into the reciprocating piston engine, wherein the splitting unit is arranged in the truck or omnibus, in particular between a tank and the reciprocating piston engine. The synthesis gas can increase the ignitability of the methanol fuel, and can thus contribute to an even more efficient operation of the reciprocating piston engine.

Another aspect of the invention relates to a truck or omnibus with a drive system, wherein the drive system comprises a power generator, at least one drive battery, and at least one electric motor, which draws electrical energy from the drive battery. The power generator comprises a two-cylinder reciprocating piston engine with two cylinder-piston units in a tandem arrangement, and at least one generator for the generation of electrical energy, wherein each cylinder-piston unit has a crankshaft, and the crankshafts of both cylinder-piston units are mechanically coupled to one another, and wherein at least one crankshaft, in particular both crankshafts, is in each case mechanically connected to the at least one generator.

The two-cylinder reciprocating piston engine is preferably customised for operation with methanol, in particular regeneratively-produced methanol, as the main fuel. The electric motor preferably operates, via a gearbox or directly, on a wheel axle. Furthermore, a tank can be provided, which is fluidically connected to the two-cylinder reciprocating piston engine, and is at least partially, preferably completely, filled with regeneratively-produced methanol. It is possible that the drive system has a plurality of power generators, each of which is electrically connected to a common drive battery, or to a plurality of separate drive batteries.

It is particularly preferred if the two-cylinder reciprocating piston engine of the above-described truck or omnibus is operated in accordance with the above-described method.

BRIEF DESCRIPTION OF THE DRAWINGS

The invention is explained in more detail by means of examples of embodiment with reference to the attached schematic drawings that have further details.

In these.

In what follows, the same reference numbers are utilised for the same parts, and for parts operating in the same manner.

DESCRIPTION

Figure 1:
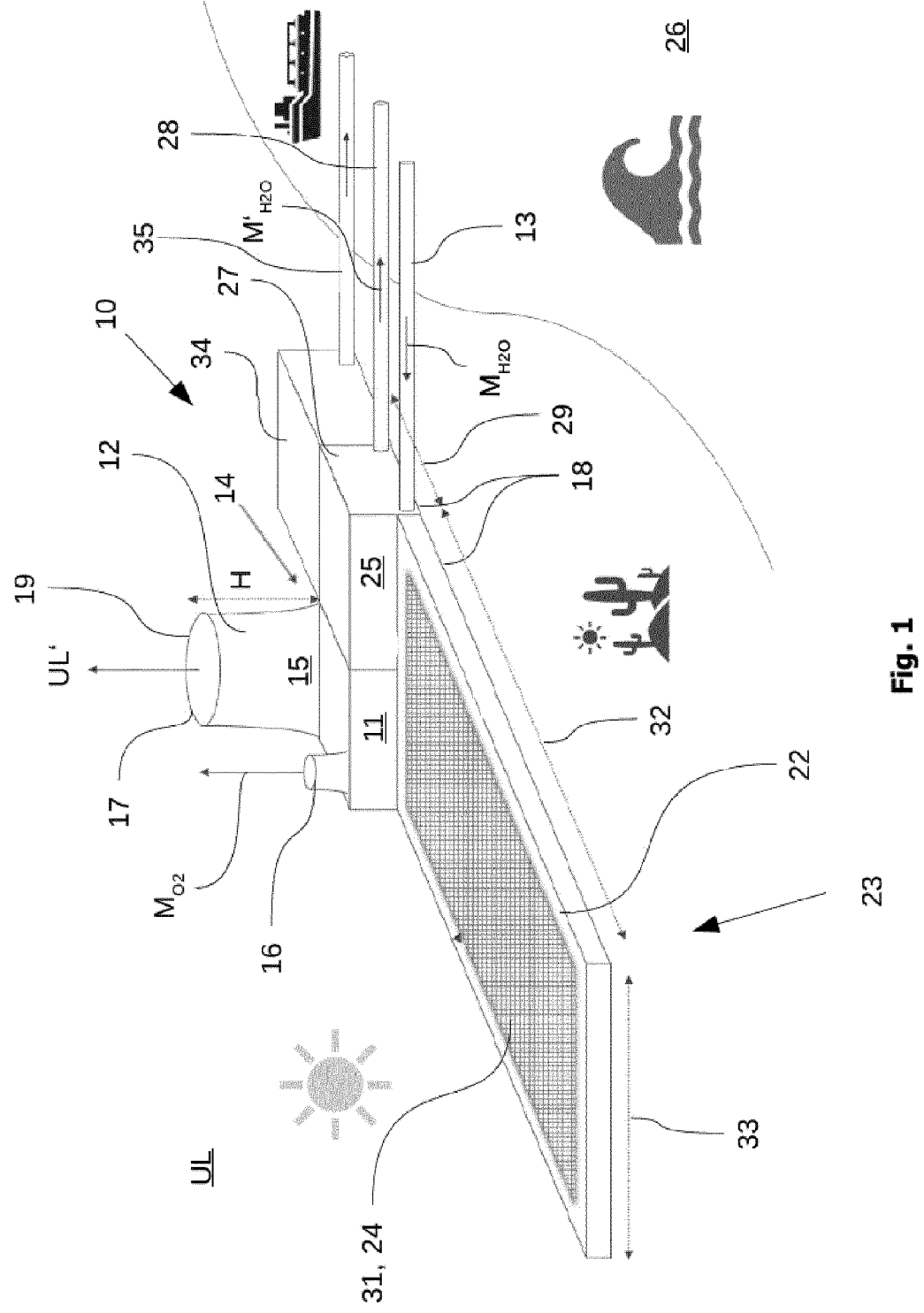
FIG. 1 shows a perspective view of a plant for the production of a globally usable energy source, in accordance with a preferred example of embodiment of the invention.

FIG. 1 shows the example of embodiment of a plant 10 that is designed for the production of a globally usable energy source in the form of methanol. The plant 10 comprises an electrolysis unit 11, a carbon dioxide sorption unit 12, a seawater desalination unit 27, and a methanol synthesis unit 34. A photovoltaic unit 24 is provided for the supply of power to the aforementioned units; this is electrically connected to the corresponding units 11, 12, 27, 34.

As can be seen in FIG. 1, the aforementioned plant components are arranged on a contiguous plant site, such that the exchange of material and energy flows between the various units and the power supply takes place with the lowest possible losses. The shape of the plant is not limited to the shape shown in FIG. 1.

The electrolysis unit 11 is connected to the seawater desalination unit 27 by at least one pipe (not shown) for the supply of water, in particular desalinated water. The desalinated water is supplied to the electrolysis unit 11 through the pipeline. The methanol synthesis unit 34 is connected, on the one hand, to the electrolysis unit 11 by at least one pipeline, and, on the other hand, to the carbon dioxide sorption unit 12 by at least one further pipeline. The hydrogen produced in the electrolysis unit 11, and the carbon dioxide separated out in the carbon dioxide sorption unit 12, are fed to the methanol synthesis unit 34 through the two pipelines. Methanol is thereby produced in the methanol synthesis unit 34.

The seawater desalination unit can be designed to receive and desalinate at least 900,000 tonnes of seawater per year. The carbon dioxide sorption unit can be customised to have an extraction capacity of at least 400,000 tonnes of carbon dioxide per year, in particular at least 600,000 tonnes of carbon dioxide per year, extracted from the ambient air. The methanol synthesis unit 34 is customised to produce at least 300,000 tonnes, in particular 450,000 tonnes, of regeneratively-produced methanol per year.

The photovoltaic unit 24 can have a power of approx. 1.5 GW and, depending on the solar radiation, can absorb at least 1,500 kWh/m²a. For the location in the Middle East selected in FIG. 1, the photovoltaic unit 24 is preferably customised to absorb at least 2,500 kWh/m²a.

The electrolysis unit 11 is designed to separate a quantity of water MH2O by electrolysis into an oxygen component MO2, and a hydrogen component. The electrolysis unit 11 thus forms a unit for water electrolysis. The electrolysis unit 11 is connected to a water supply line 13 for the reception of the quantity of water MH2O. As can be seen in FIG. 1, a pump unit 25 is arranged between the electrolysis unit 11 and the water supply line 13. The pump unit 25 has at least one pump for the transportation of water from a water reservoir 26. The water reservoir 26 can be a sea with seawater. Alternatively, the water reservoir 26 can be a lake with fresh water. It is also possible that the water supply line 13 is connected to a river so as to draw fresh water for water electrolysis. In the plant 10 shown in FIG. 1, the water supply line 13 is connected to a sea for the extraction of seawater. The plant 10 is preferably located near the coast so as to keep the distance to be covered for the water supply short, in particular to keep the water supply line 13 short.

The pump unit 25 is designed for the purpose of pumping seawater from the sea and making it available to further sub-plants or units for further processing. In order to prepare the seawater for the electrolysis process undertaken by the electrolysis unit 11, the plant 10 has a seawater desalination unit 27. The seawater desalination unit 27 is connected to the pump unit 25 by at least one pipe. The seawater desalination unit 27 is customised to separate out a certain amount of salt from the quantity of seawater MH2O delivered, so that the seawater has a reduced salt content after the desalination process by the seawater desalination unit 27. The desalinated quantity of seawater MH2O corresponds to the quantity of water MH2O, which is separated into an oxygen component MO2 and a hydrogen component by the electrolysis unit 11. The electrolysis unit 11 is connected to the seawater desalination unit 27 by at least one pipe. In order to convey the desalinated seawater from the seawater desalination unit 27 to the electrolysis unit 11, at least one further pump can be connected in between.

As described above, the electrolysis unit 11 is customised to separate the absorbed quantity of water MH2O into a hydrogen component and an oxygen component MO2. The hydrogen component is supplied to the methanol synthesis unit 34. The oxygen component MO2 is discharged into the environment. The electrolysis unit 11 is preferably customised to separate out an oxygen component MO2 of at least 1.2 kg and a hydrogen component of at least 0.15 kg, in particular of 0.19 kg, from an absorbed quantity of water MH2O of at least 1.5 kg. For purposes of discharging the produced oxygen component MO2, the electrolysis unit 11 has an oxygen outlet 16 which opens out into the external atmosphere. The plant 10 has a hydrogen transport device (not shown) for the supply of the hydrogen to the methanol synthesis unit 34.

It is possible for the plant 10 to have a hydrogen storage unit, such that the methanol synthesis unit 34 can be supplied with hydrogen as continuously as possible.

As shown in FIG. 1, the carbon dioxide sorption unit 12 has an air inlet 14 for the supply of ambient air UL, and a downstream sorber device 15. It is possible for the carbon dioxide sorption unit 12 to have one or more air inlets 14. The sorber device 15 is connected to the air inlet 14. The sorber device 15 is customised so as to extract a quantity of carbon dioxide from the ambient air UL. The carbon dioxide sorption unit 12 furthermore has an air outlet 17 that is oriented upwards in the vertical direction. The air outlet 17 serves to discharge the exhaust air UL', whose carbon dioxide concentration is lower than the carbon dioxide concentration of the ambient air UL. The air outlet 17 is part of a stack 19.

More specifically, the sorber device 15 is arranged between the air inlet 14 and the air outlet 17. In operation, the ambient air UL flows through the air inlet 14 to the sorber device 15, which separates out, in particular filters out, a certain amount of carbon dioxide from the air UL, wherein downstream of the sorber device 15 the filtered exhaust air UL' flows through the air outlet 17 into the external atmosphere. In general, it is possible for a plurality of air inlets 14, a plurality of sorber devices 15, and a plurality of air outlets 17, to be provided.

More specifically, FIG. 1 shows a single stack 19 with a height H of 200 metres, which shows in an exemplary manner the external structure of the carbon dioxide sorption unit 12. The air outlet 17 opens into the external atmosphere, as shown in FIG. 1, in the same manner as the oxygen outlet 16.

The plant 10 further comprises a carbon dioxide transport device (not shown), which is designed for purposes of making the carbon dioxide quantity separated out from the ambient air UL available to a carbon dioxide storage unit, and/or to the methanol synthesis unit 34, for further processing. The carbon dioxide storage unit serves to ensure as continuous a supply of carbon dioxide as possible to the methanol synthesis unit 34.

The carbon dioxide sorption unit 12 can have an extraction capacity of an amount of carbon dioxide per year of at least 400,000 tonnes, in particular 600,000 tonnes. In other words, the carbon dioxide sorption unit 12 can be customised to process an ambient quantity of air per year of at least 1,500 megatonnes. More specifically, the carbon dioxide sorption unit 12 is preferably customised to extract a carbon dioxide quantity of at least 1.4 kg from an ambient quantity of air of at least 3,300 kg.

As shown in FIG. 1, the plant 10 has a planar plant area 23. The planar plant area 23 is directly adjacent to the electrolysis unit 11. A power generation unit 31, which is a photovoltaic unit 24, is arranged on the planar plant area 23. The photovoltaic unit 24 is connected to the respective units of the plant 10 for purposes of power supply. The photovoltaic unit 24 is customised in such a manner that the entire installation 10 can be operated self-sufficiently in terms of energy. This is to be understood as meaning that the electrical power for operating the entire plant 10 can be provided exclusively by solar energy by means of the photovoltaic unit 24. In other words, it is preferable that no fossil energy sources are utilised for the operation of the plant 10.

The planar plant area 23 can have a longitudinal extent 32 of approximately 5,000 metres and a transverse extent 33 of approximately 2,000 metres. In other words, the planar plant area of the plant 10 preferably covers an area of 10 square kilometres. The plant area shown in FIG. 1 containing the electrolysis unit 11 can have a longitudinal sub-extent 29 of approximately two kilometres. Other longitudinal sub-extents, and longitudinal and transverse extents, 29, 32, 33 are possible.

The seawater desalination unit 27 described above is connected to a water return line 28, through which a returnable quantity of seawater M'H2O with an increased salt content is returned to the sea. More specifically, a certain salt content is extracted from the extracted quantity of seawater, and is then returned to the sea with a proportion of the extracted quantity of seawater as a returnable quantity of water M'H2O. This provides a water cycle that is not damaging to nature.

The preferred installation site of the plant 10 is near the coast of a sea. Particularly preferably, the plant 10 is set up in a desert. A methanol delivery line 35 can connect the plant 10 to a methanol delivery point, for example in a port.

The plant 10 as shown in FIG. 1 is a large power plant. The plant 10 can have at least one installation area 18 that is connected to a foundation of a building and/or a structure. In general, it is possible for the electrolysis unit 11 and/or the carbon dioxide sorption unit 12 to be arranged in a common building, or in separate buildings.

The power supply unit 31 preferably has a power storage unit (not shown), which is customised to supply power to the plant 10 during night-time operation.

Figure 2:
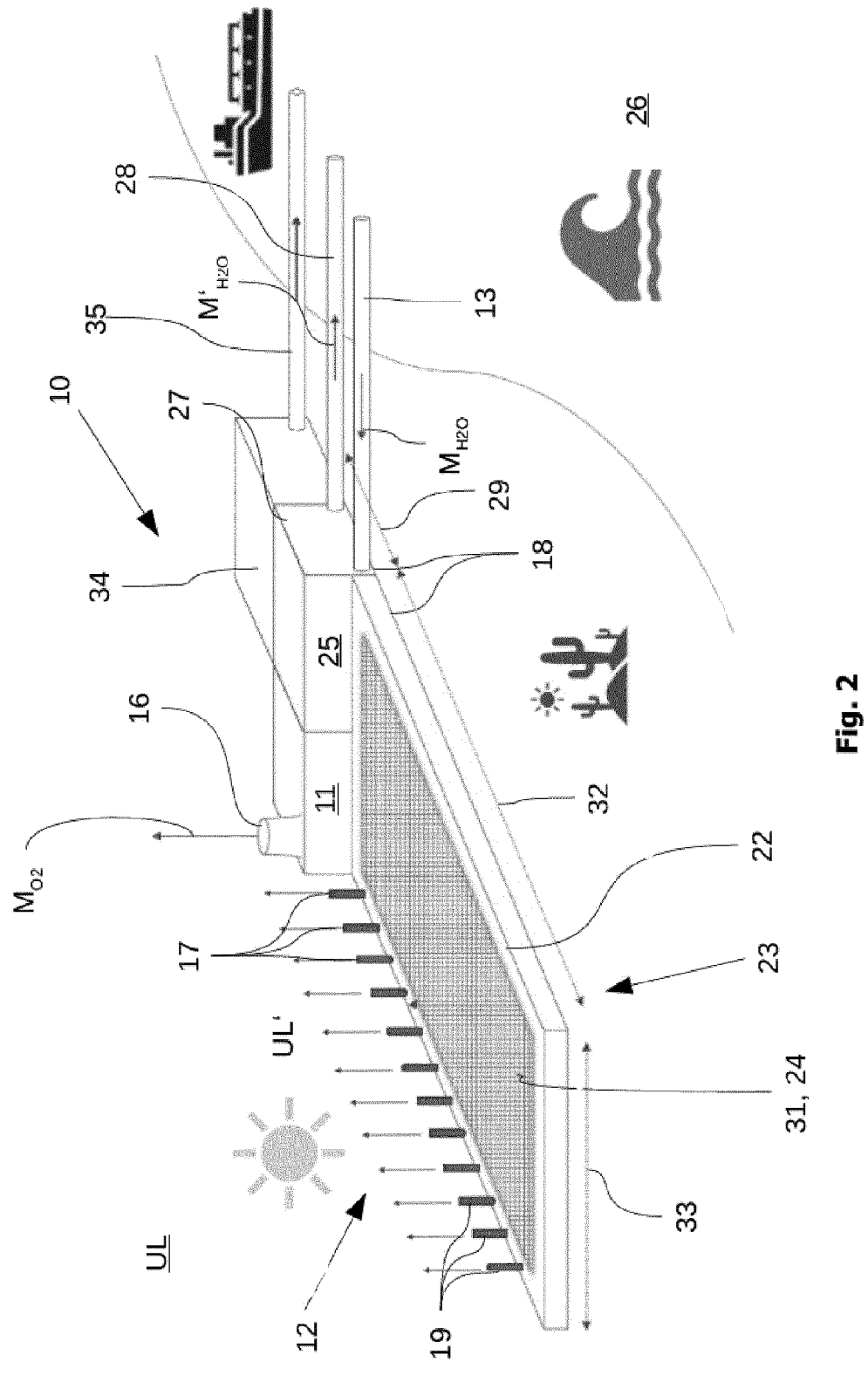
FIG. 2 shows a perspective view of a plant for the production of a globally usable energy source, in accordance with a further preferred example of embodiment in accordance with the invention.

In contrast to FIG. 1, FIG. 2 shows a plant 10 in which the single carbon dioxide sorption unit 12 is replaced by a plurality of carbon dioxide sorption units 12. The particular carbon dioxide sorption unit 12 shown in FIG. 2 has a stack 19 and a flow channel 21 extending transversely to the stack 19. This is clearly visible in FIG. 4, for example. The flow channel 21 is connected to the stack 19 in a region of the stack arranged at the bottom of the structure when installed. A sorber device 15 is arranged between the flow channel 21 and the stack 19; this is designed to extract a quantity of carbon dioxide from the ambient air UL. The sorber device 15 is formed by an amine exchanger. Other types of sorber devices are possible.

Figure 3:
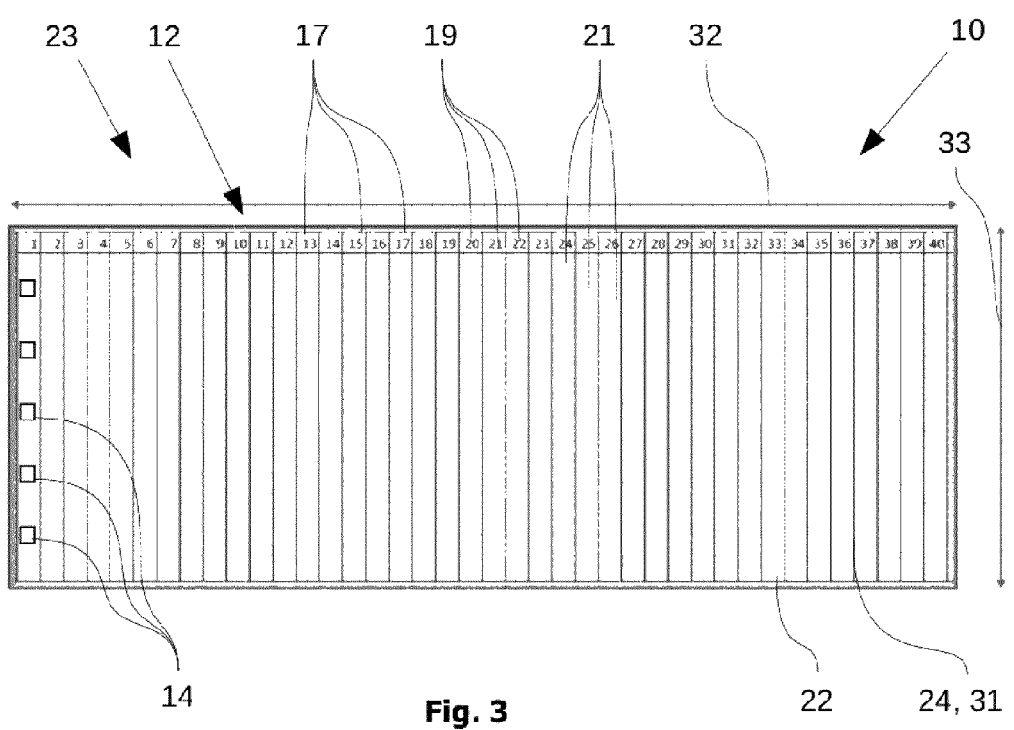
FIG. 3 shows a plan view onto a planar plant area of the plant shown in FIG. 2.

As FIGS. 2, 3 show, the stacks 19 are arranged along the longitudinal extent 32 of the planar plant area 23. The planar plant area 23 has a surface 22 arranged at the top of the structure when installed. The surface 22 arranged at the top of the structure is dark in colour, at least in some sections, in order to absorb solar energy. The flow channels 21 are arranged below the upper surface 22 when installed. A plurality of air inlets 14 are formed in the upper surface 22 to supply ambient air UL into the flow channels 21. The air inlets 14 form passage openings through the upper surface 22. For the sake of clarity, these are only shown on the first flow channel 21 in FIG. 3. The number of air inlets 14 is also variable.

In operation, ambient air flows through the air inlets 14 into the flow channel 21 and then through the sorber device 15. Downstream of the sorber device 15, the exhaust air UL' with reduced carbon dioxide concentration flows into the stack 19, and through the air outlet 17 into the external atmosphere. By virtue of the dark-coloured surface 22 arranged at the top of the structure, the ambient air located below the surface 22 in the flow channel 21 heats up during operation. The temperature of the ambient air UL in the flow channel 21 is preferably approx. 60° C. With an external temperature of the ambient air UL of approx. 40° C., natural ventilation is created by the arrangement of the stack with the flow channel 21, together with the dark-coloured surface 22. In other words, no fan or blower is necessary for the supply of the ambient air UL into the flow channel 21, or for the flow through the sorber device 15, or for the outflow of the purified ambient air UL' from the stack 19.

FIG. 3 shows a plan view onto the planar plant area 23 of the plant 10 shown in FIG. 2. The numbering from 1 to 40 shown along the longitudinal extent 32 represents the number of stacks 19 arranged along the longitudinal extent 32. The lines running transversely to the longitudinal extent 32 show schematic separations between the individual flow channels 21. The individual flow channels 21 are in each case assigned to a stack 19. At the same time a sorber device 15 is in each case arranged between the flow channel 21 and the stack 19. The longitudinal extent 32 of the two-dimensional plant area 23 is approximately 5,000 metres and the transverse extent 33 of the planar plant area 23 is approximately 2,000 metres. A total of forty stacks 19 with a total of forty flow channels 21 are provided in the planar plant area 23. These have a combined delivery of exhaust air UL' of at least 1,800 megatonnes per year.

To achieve this, the stacks 19 have a diameter D that is 25 metres. The diameter D refers to the region of the stack 19 in which the air outlet 17 is formed. The air outlet 17 is formed at a free end of the stack 19. Furthermore, the stack in question 19 has a height H of 100 metres. By this means an optimal shape is formed for the stack so as to provide natural ventilation. Other dimensions of the stacks 19 are possible.

Furthermore, more than, or less than, forty stacks 19, in each case with an associated flow channel 21, can be arranged in the planar plant area 23.

Figure 4:
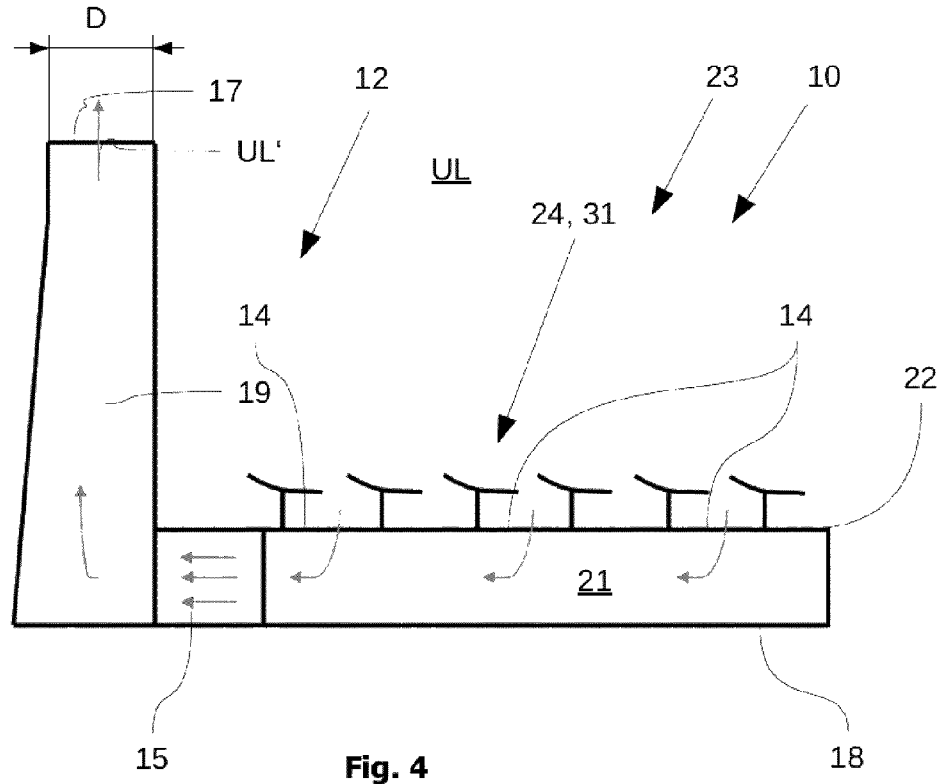
FIG. 4 shows a schematic cross-section through the planar plant area of the plant shown in FIG. 3.

As can be seen in FIG. 4, the planar plant area 23 is provided with a photovoltaic unit 24 on the surface 22 arranged at the top of the structure. In other words, a photovoltaic unit 24 is arranged on the upper surface 22 of the planar plant area 23. The photovoltaic unit 24 preferably delivers 1.5 gigawatts per year. In the plant 10 shown in FIG.

2, the carbon dioxide sorption unit 12 and the photovoltaic unit 24 thereby spatially form a common unit. The photovoltaic unit 24 forms a power supply unit 31 for the energy-autonomous operation of the entire plant 10.

It should be noted that the above-described plants 10, shown in FIGS. 1 and 2, are identical except for the differences that have been described.

Figure 5:
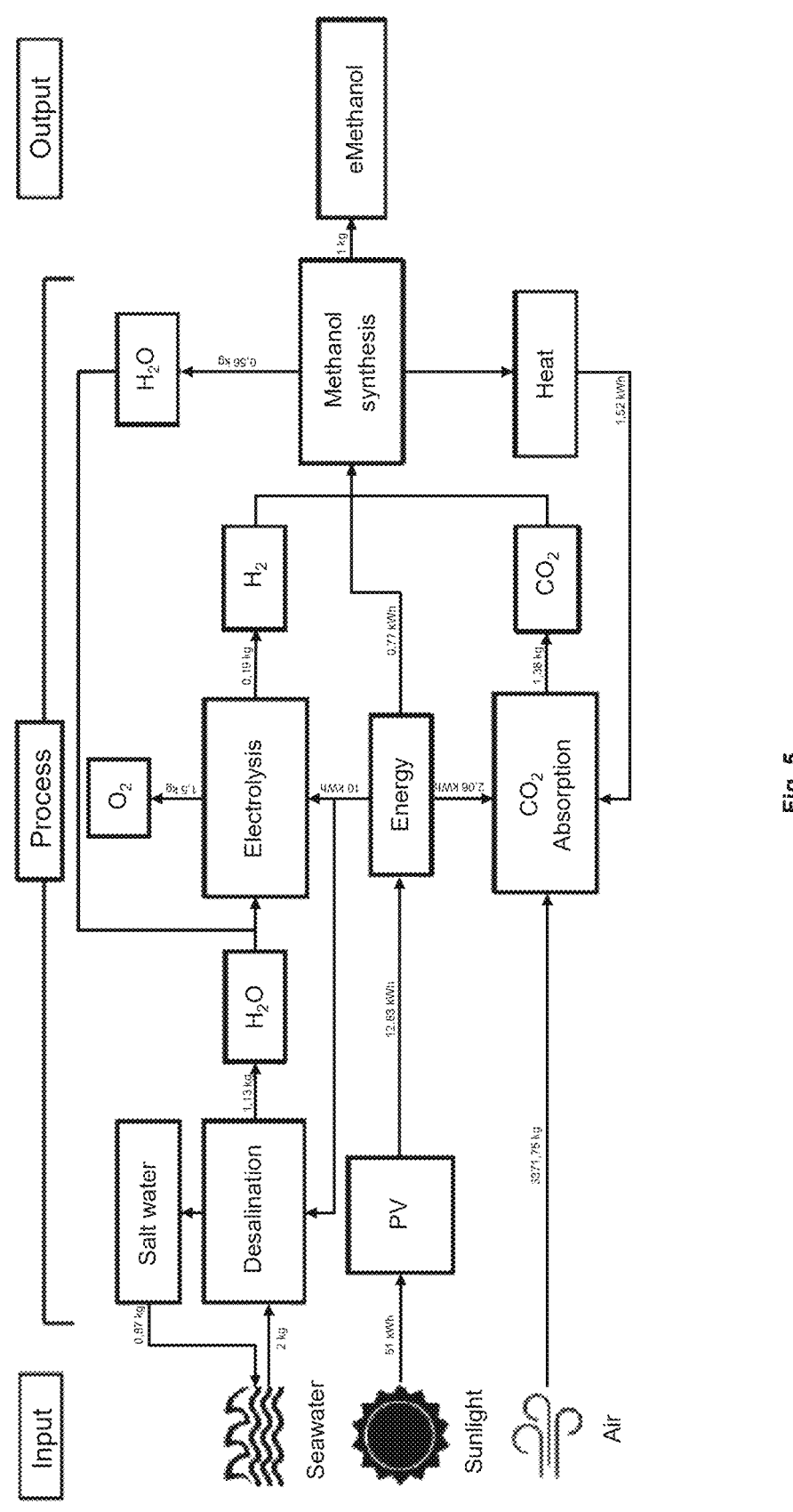
FIG. 5 shows a flow diagram of the method for the production of a globally usable energy source with the plant shown in FIG. 1, or the plant shown in FIG. 2.

The method that can be carried out with the plant 10 shown in FIG. 1 or FIG. 2 is explained with the aid of the flow chart shown in FIG. 5:

To produce a quantity of 1 kg of methanol, a quantity of approximately 2 kg of seawater is fed to the plant 10 and desalinated in the seawater desalination unit 27. This generates approx. 1.13 kg of desalinated water. The residual salt water (approx. 0.87 kg) is returned to the sea through the water return line 28. In the electrolysis unit, the desalinated water and, if necessary, further quantities of water produced in later process steps, are split into hydrogen (approx. 0.19 kg) and oxygen (approx. 1.5 kg). The carbon dioxide sorption unit 12 takes in a quantity of air of approx. 3,371.75 kg through the air inlet 14 and extracts a quantity of approx. 1.38 kg of carbon dioxide from the unit. Hydrogen and carbon dioxide are fed to the methanol synthesis unit, where they are processed into 1 kg of methanol. The excess heat generated during the synthesis is fed to the carbon dioxide sorption unit 12. The synthesis also produces a quantity of water of approximately 0.56 kg, which is fed to the electrolysis unit. For these process steps, approx. 51 kWh of solar energy is converted into approx. 12.83 kWh of usable electricity energy by the photovoltaic system.

Figure 6:
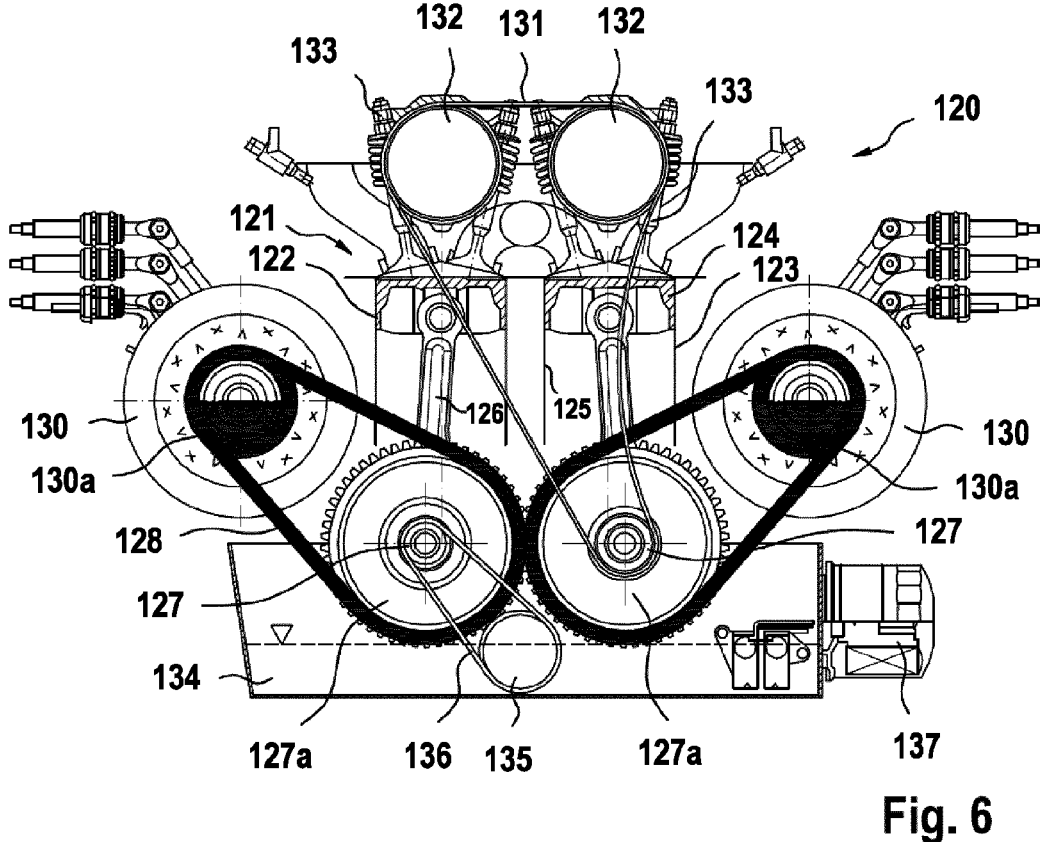
FIG. 6 shows a cross-sectional view of a power generator of a truck or omnibus in accordance with the invention, in a preferred example of embodiment.

FIG. 6 shows a power generator 120 for a truck or omnibus in accordance with the invention. The power generator 120 comprises a two-cylinder reciprocating piston engine 121, with a first cylinder-piston unit 122 and a second cylinder-piston unit 123. Each of the cylinder-piston units 122, 123 comprises a piston 124 guided in a cylinder 125. The piston 124 is coupled to a connecting rod 126, which connects the piston 124 to a crankshaft 127. The crankshafts 127 are aligned parallel to each other, and in each case carry spur gears 127a, which have external teeth. The externally-toothed spur gears 127a mesh with each other such that the spur gears 127a rotate in opposite directions.

Each spur gear 127a is coupled to a generator 130 via a toothed belt 128. A total of two generators 130 are provided. The generators 130 also include balance weights 130a, which balance out the mass forces and the mass moments.

The power generator 120 furthermore comprises a cam belt 131, which connects one of the crankshafts 127 to camshafts 132. Each cylinder-piston unit 122, 123 is associated with a respective camshaft 132. The camshafts 132 in each case act on valves 133, wherein each cylinder-piston unit preferably has four valves 133.

Furthermore, an oil sump 134 is provided, in which an oil pump 135 is arranged. The oil pump 135 is driven by an oil pump belt 136, which connects the oil pump 135 to one of the crankshafts 127. The oil pump 135 is preferably connected to another crankshaft 127, rather than the camshafts 132. Furthermore, an oil filter 137 is arranged in the oil sump 134.

As can be seen in FIG. 6, the power generator 120 has a particularly compact design. It has relatively few parts and is therefore easy to maintain and has a low weight. The two-cylinder reciprocating piston engine is particularly low in noise and vibration. In addition, the two-cylinder reciprocating piston engine can be encapsulated in a housing, wherein the housing can additionally contribute to low noise and low vibration. The propulsion system of a truck or omnibus can include a plurality of power generators 120 that act together to generate power, and feed drive batteries.

FIG. 6 also shows that the cylinders 125 of the cylinder piston units 122, 123 are arranged in an interfaced manner. In particular, the central axes of the cylinders 125 have a smaller distance from each other than the central axes of the crankshafts 127. As a result, the connecting rods 126 are slightly inclined to each other at top dead centre of the pistons 124, as shown in FIG. 6. This massively reduces vibrations when the engine is started. In particular, when starting the power generator 120, start-up mass moments are reduced in this manner, so that the otherwise familiar start-up vibrations do not occur.

For the propulsion of a truck or omnibus, the power generator 120 is preferably operated, and provides via the generators 130 the electrical energy that is required in order to use the electric motors in drive mode. A 48 volt, 400 volt or 800 volt, system is preferably integrated as the electrical system. The drive batteries are preferably dimensioned such that the truck or omnibus can travel between 10 km and 120 km, in particular between 20 km and 100 km, in particular between 25 km and 60 km, in an exclusively electrical manner, that is to say, without operation of the power generator.

The power generator 120 is preferably powered by the regeneratively-produced methanol. For this purpose, an appropriate tank is provided, which accommodates the regeneratively-produced methanol, that is to say, is filled with the latter. In this manner, a particularly economical and at the same time climate-friendly operation of the truck or omnibus is possible.

As explained with the aid of the above examples of embodiment, the invention offers a technically feasible and economical solution to the acute climate problem, which can be implemented within a reasonable time frame by virtue of the scalability of the described systems. The invention takes into account the geographical opportunities offered by certain regions of the world, and has an impressive simplicity.

LIST OF REFERENCE SYMBOLS

10 Plant
11 Electrolysis unit
12 Carbon dioxide sorption unit
13 Water supply line
14 Air inlet
15 Sorber device
16 Oxygen outlet
17 Air outlet
18 Installation area
19 Stack
21 Flow channel
22 Surface arranged at the top of the structure
23 Planar plant area
24 Photovoltaic unit
25 Pump unit
26 Water reservoir
27 Seawater desalination unit
28 Water return line
29 Longitudinal sub-extent
31 Power generation unit
32 Longitudinal extent
33 Transverse extent
34 Methanol synthesis unit
35 Methanol delivery line
120 Power generator
121 Two-cylinder reciprocating piston engine

122 First cylinder-piston unit
123 Second cylinder-piston unit
124 Piston
125 Cylinder
126 Connecting rod
127 Crankshaft
127a Spur gear
128 Toothed belt
130 Generator
130a Balance weight
131 Cam belt
132 Camshaft
133 Valve
134 Oil sump
135 Oil pump
136 Oil pump belt
137 Oil filter
UL Ambient air with increased carbon dioxide concentration
UL' Exhaust air with lowered carbon dioxide concentration
D Diameter
H Height
MH2O Quantity of water extracted
M'H2O Quantity of water recirculated
MO2 Oxygen component

The invention claimed is:

1. A method for operating an internal combustion engine of a truck or bus having at least a 3.5 tonne total mass comprising: splitting water into hydrogen and oxygen in an electrolysis unit configured for production of hydrogen; extracting carbon dioxide from ambient air at a carbon dioxide sorption unit; feeding the hydrogen and the carbon dioxide to a methanol synthesis unit configured for the production of methanol, wherein the methanol synthesis unit synthesizes the hydrogen and the carbon dioxide into methanol; and converting absorbed solar energy at a photovoltaic unit into electrical energy, wherein the electrolysis unit, the carbon dioxide sorption unit and the methanol synthesis unit are operated by the electrical energy generated in the photovoltaic unit, wherein the methanol is transported by a distribution system to a tank of the truck or bus, and wherein the methanol is supplied from the tank as fuel for combustion to the internal combustion engine for generation of mechanical energy to a hybrid drive train of the truck or bus, wherein the water is desalinated in a seawater desalination unit and fed to the electrolysis unit, wherein the seawater desalination unit is operated by the electrical energy generated in the photovoltaic unit, wherein a hydrogen storage unit enables feeding the methanol synthesis unit with hydrogen continuously, wherein the carbon dioxide sorption unit maintains a closed-loop carbon dioxide cycle with the ambient air and methanol combustion with carbon neutrality.

2. The method according to claim 1, further comprising: splitting part of the methanol into a synthesis gas including hydrogen and carbon monoxide at a splitting unit arranged in the truck or bus; and feeding the synthesis gas into a reciprocating piston engine.

3. A truck or bus comprising:
a drive system and a tank at least partially filled with methanol regeneratively-produced by, an electrolysis unit configured to split water into hydrogen and oxygen for production of hydrogen;
a carbon dioxide sorption unit configured to extract carbon dioxide from ambient air;

a methanol synthesis unit configured for the production of methanol using a supply of the hydrogen and the carbon dioxide, wherein the methanol synthesis unit synthesizes the hydrogen and the carbon dioxide into the regeneratively produced methanol, wherein a hydrogen storage unit enables feeding the methanol synthesis unit with the hydrogen continuously; and a photovoltaic unit configured to convert absorbed solar energy into electrical energy, wherein the electrolysis unit, the carbon dioxide sorption unit and the methanol synthesis unit are operated by the electrical energy generated in the photovoltaic unit, and wherein the drive system is powered by a reciprocating engine fueled by the regeneratively produced methanol, wherein the carbon dioxide sorption unit maintains a closed-loop carbon dioxide cycle with the ambient air and the methanol combustion with carbon neutrality.

4. The truck or bus according to claim 3 wherein the drive system comprises a power generator, at least one drive battery, and at least one electric motor adapted to draw electrical energy from the drive battery.

5. The truck or bus according to claim 4 wherein the electric motor operates via one of a gearbox or directly on a wheel axle of the truck or bus.

6. The truck or bus according to claim 4 wherein the power generator includes the reciprocating engine having two cylinder-piston units in a tandem arrangement, and at least one generator configured for generation of electrical energy.

7. The truck or bus according to claim 6 wherein the tank is fluidically connected to the two-cylinder reciprocating piston engine.

8. The truck or bus according to claim 7 wherein each cylinder-piston unit has a crankshaft, and wherein the crankshaft of each cylinder-piston unit is mechanically coupled to one another.

9. The truck or bus according to claim 8 wherein at least one crankshaft is mechanically connected to the at least one generator.

10. The truck or bus according to claim 3 further comprising a splitting unit wherein part of the methanol is split into a synthesis gas comprising hydrogen and carbon monoxide, and wherein the synthesis gas is fed alone, or together with the methanol, into the reciprocating engine, and wherein the splitting unit is arranged between a tank and the reciprocating engine.

11. The method of claim 1, wherein carbon dioxide is reduced as a greenhouse gas from the ambient air.

12. The truck or bus of claim 3, wherein carbon dioxide is reduced as a greenhouse gas from the ambient air.

* * * * *